(12) United States Patent
Renner

(10) Patent No.: US 10,365,245 B2
(45) Date of Patent: Jul. 30, 2019

(54) GATING ELEMENT IN ION MOBILITY SPECTROMETERS

(71) Applicant: Bruker Daltonik GmbH, Bremen (DE)

(72) Inventor: Uwe Renner, Leipzig (DE)

(*) Notice: Subject to any disclaimer, the term of this patent is extended or adjusted under 35 U.S.C. 154(b) by 0 days.

(21) Appl. No.: 15/846,861

(22) Filed: Dec. 19, 2017

(65) Prior Publication Data
US 2018/0196003 A1    Jul. 12, 2018

(30) Foreign Application Priority Data

Dec. 20, 2016 (DE) .......................... 10 2016 124 900

(51) Int. Cl.
*G01N 27/62* (2006.01)

(52) U.S. Cl.
CPC .................................. *G01N 27/622* (2013.01)

(58) Field of Classification Search
CPC .................................................. G01N 27/622
USPC .............................. 250/281, 282, 283, 288
See application file for complete search history.

(56) References Cited

U.S. PATENT DOCUMENTS

| 7,081,621 | B1* | 7/2006 | Willoughby | H01J 49/04 250/283 |
|---|---|---|---|---|
| 7,417,222 | B1 | 8/2008 | Pfeifer et al. | |
| 8,198,584 | B2 | 6/2012 | Renner | |
| 8,304,717 | B2 | 11/2012 | Renner | |
| 8,658,972 | B2* | 2/2014 | Zhang | G01N 27/622 250/281 |
| 2002/0011560 | A1* | 1/2002 | Sheehan | H01J 49/067 250/283 |
| 2004/0245458 | A1* | 12/2004 | Sheehan | H01J 49/067 250/288 |
| 2005/0258363 | A1* | 11/2005 | Syms | G01N 27/624 250/292 |
| 2008/0179515 | A1 | 7/2008 | Sperline | |
| 2010/0320375 | A1 | 12/2010 | Renner | |
| 2011/0062323 | A1* | 3/2011 | Brown | H01J 49/0072 250/282 |
| 2013/0009050 | A1* | 1/2013 | Park | H01J 49/063 250/281 |
| 2015/0108345 | A1 | 4/2015 | Fujita | |

FOREIGN PATENT DOCUMENTS

| EP | 1676291 B1 | 5/2005 |
|---|---|---|
| WO | 2015194943 A1 | 12/2015 |

* cited by examiner

*Primary Examiner* — Nicole M Ippolito
(74) *Attorney, Agent, or Firm* — Benoit & Côté Inc.

(57) ABSTRACT

The invention relates to a gating element for switching or modulating the ion current in ion mobility spectrometers, particularly in miniature ion mobility spectrometers (IMS) operated at atmospheric pressure, where the ion current of an ion source is modulated with a continuous modulation function and the mobility spectrum is generated from the measured ion current by a correlation analysis with the modulation pattern. The invention proposes using a layered plate with apertures (apertured plate) rather than a grid (or a series of grids), said apertured plate comprising at least three conductive and two insulating (or low-conductivity) layers arranged alternately, which are firmly bonded with each other.

15 Claims, 5 Drawing Sheets

GATING ELEMENT IN ION MOBILITY SPECTROMETERS

BACKGROUND OF THE INVENTION

Field of the Invention

The invention relates to a gating element for modulating or switching of ion currents in ion mobility spectrometers (IMS) wherein, in particular, the ion current of an ion source is modulated with a continuous modulation function and the mobility spectrum is generated from the measured ion current by a correlation analysis with the modulation pattern.

Description of the Related Art

In most cases, ion mobility spectrometers are operated by injecting very short ion current pulses. A conventional ion mobility spectrometer for the measurement of pollutants, drugs or explosives in air is shown in FIG. 1. The ions are generated continuously in an ion source (2) and then introduced into the drift region of the spectrometer by a gating grid (4) over a short time span. The time spans for the transmission are usually between 100 and 300 microseconds, and the acquisition of the spectrum takes around 30 milliseconds. Bipolar wire grids according to Bradbury-Nielsen are often used as gating grids.

The ions transmitted by the grid (4) are then drawn by an axial electric field through a collision gas in a drift region (8) to the Faraday detector (9). Their velocity is determined by their "mobility", which in turn depends in a known way on their collision cross-section, their mass, their ability to become polarized, and their tendency to form complex ions with molecules from the collision gas. The drawing field is formed by a series of electrodes (7), which surround the drift region (8) and to which linearly increasing or decreasing potentials are applied, depending on the electric charge of the ions. From the molecules of a substance which enters the ion source (2) together with ambient air (1), several ionic species are formed in the ion source (2), such as monomers, dimers and complex ions with water and collision gas molecules, usually in complex series of ionization reactions, for example by means of radioactive radiation from an emitter (3). Each ionic species has its own characteristic mobility. At the end of the drift region (8), the incident ion current is measured with an ion detector (9), digitized and saved as a "mobility spectrum" in the form of a digitized sequence of measured values. An evaluation of this mobility spectrum provides information on the mobility of the ions involved and hence indications as to the substances involved. (There are also ion sources which operate without radioactivity).

The method is extraordinarily sensitive in respect of certain groups of substances and is largely used for the measurement of pollutants in air, for example for monitoring of chemical laboratories, for continuous monitoring of filters, for control of drying processes, for monitoring of waste air, and for detection of chemical warfare agents, explosives, drugs, and so forth.

For a conventional spectral measurement repetition rate of about 30 spectra per second, and an ion transmission time of between 150 and 300 microseconds, only between one-half and one percent of the ions of a substance which is introduced in gas phase state are actually utilized. The remaining ions are discharged, predominantly at the gating grid (4), and are lost to the measurement process.

The patent specification DE 10 2008 015 000 B4 (U. Renner; GB 2 458 368 B; U.S. Pat. No. 8,304,717 B2) describes a method in which the ion current in the ion mobility spectrometer is modulated at the gating element (4) by a continuous modulation function, and the mobility spectrum is generated from the measured ion current by means of a correlation analysis with the modulation pattern. Preferably, a gating element (4) is used for the modulation which comprises a characteristic that is as linear as possible, since otherwise interfering sidebands occur, which could wrongly be assumed to be real signals. A favorable modulation function is a "chirp", i.e., a sine function whose frequency is continuously tuned from a lower limit to an upper limit and repeated periodically in a continuous measurement mode.

The patent specification DE 10 2009 025 727 B4 (U. Renner; GB2471745B; U.S. Pat. No. 8,198,584 B2) explains how interfering sidebands in the mobility spectrum, which are generated as a result of the non-linear behavior of the modulating gating element (4), can be reduced by a systematically pre-distorted modulation function. It is nevertheless advantageous to use a gating element (4) with a characteristic which is as straight as possible.

The conventional bipolar, coplanar wire grids according to Bradbury-Nielsen are not advantageous for the analog modulation because the transverse fields between the wires cause a lateral deflection of the migrating ions. It is better to use two (or more) unipolar gating grids in series, whose counter voltages or attracting voltages act essentially in the axial direction. They are known as "Tyndall-Powell gates".

The published patent application US 2008/0179515 A1 (R. P. Sperline, 2007) describes, in particular, ion-collecting gating methods for ions in ion mobility spectrometers which comprise Tyndall-Powell gating elements with two, three or four free-standing grids and which generate short pulses of ions.

The published patent application WO 2015/194943 A1 (S. V. Mitko, 2014) discloses gating grids ("shutters") according to Tyndall-Powell with three or four grids, wherein two grids which can be supplied with different potentials are located on the front and rear of an electrode plate with elongated apertures such that two coplanar line grids result. The outermost grids are present to ensure that the field gradients in the spectrometer on both sides of the gating element are disturbed as little as possible. Operation comprises a pulsed switching on and off of the ion current to generate short ion current pulses.

The U.S. Pat. No. 7,417,222 B1 (K. B. Pfeifer and S. B. Rhode, 2005) describes a correlation ion mobility spectrometer. A gating element modulates the ion current, and the mobility spectrum is obtained by means of a correlation analysis of the ion current pattern with the modulation function. A gating grid according to Bradbury-Nielsen as well as a pair of grids according to Tyndall-Powell are proposed as the gating element.

If a mobility spectrometer is to be miniaturized, the use of grids as gating elements is unfavorable. The necessarily very thin wires are susceptible to vibrations, which impair the switching or modulation function. It is, moreover, difficult to shape and arrange the grids such that the modulation curve created is as linear as possible.

The objective is to find a gating element with which the ion current from a continuously operating ion source of an ion mobility spectrometer can be switched or modulated, which is mechanically stable, and simple and low cost to manufacture and operate. The gating element should have a characteristic that is as linear as possible in order to suppress interfering sidebands in the mobility spectrum, especially in the case of continuous modulation of the ion current and subsequent correlation analysis of the measured ion current.

SUMMARY OF THE INVENTION

The invention provides a layered apertured plate as gating element for switching or modulating the ion current in an ion mobility spectrometer. The apertured plate comprises at least three conductive and two insulating (or low-conductivity) layers, which are preferably arranged alternately, e.g., conductive, insulating, conductive, insulating, conductive. The layers comprise solid materials, are firmly bonded to each other and have a large number of apertures which are mostly arranged such that a large number of continuous, enclosed channels are formed between the two sides of the apertured plate. The layered apertured plate thus has a large number of apertures for the passage of the ions.

The conductive layers (electrode layers) can be made of copper, silver, or other metals which conduct well, preferably with a conductivity of more than $10^6$ S/m. The non-conductive, or low-conductivity, layers (insulating layers) can be made of polyimide (Kapton™), ceramic, glass, other nonconductors or semiconductors or low-conductivity polymers, preferably with a conductivity of less than $10^5$ S/m and particularly of less than $10^3$ S/m. For example, an apertured plate according to the invention can be made of the layers copper-Kapton-copper-Kapton-copper. Bonding techniques for layers of copper and Kapton are known from the manufacture of circuit boards. According to the manufacturing process, the layered apertured plate can, for example, also comprise two or more conductive layers, which are bonded together, but are surrounded by insulating layers; or two or more insulating layers, which are bonded together, but surrounded by conductive layers. Preferably, a conductive layer is located in the interior of the apertured plate and conductive layers are located on each outer side of the apertured plate, with the conductive layers being separated by insulating layers. The apertured plate (plate) can be any shape, for example circular, with diameters of four to 15 millimeters. The thickness of the plate is preferably between 50 and 500 micrometers.

A method for producing the gating element according to the invention comprises producing the plate by calendering together or adhesively bonding conductive and non-conductive or low-conductivity films. The apertures can be produced, after the layers have been joined together, by chemical etching, by ion etching or, in particular, by laser drilling or etching, preferably with ultra-short pulse lasers (e.g. picosecond lasers or femtosecond lasers). Laser drilling with ultra-short pulse lasers facilitates precise machining because of the direct phase transition into the gas phase state without melting artifacts. The apertures can be circular, square or hexagonal and can have a diameter of between 50 and 500 micrometers. The diameter of an aperture preferably corresponds roughly to the depth of the aperture through the plate. The optical transparency of the plate can be between 10% and 90%, preferably between 30% and 70%, in particular around 50%, with the area of the apertures then roughly corresponding to half of the plate area.

The passage of ions through a layered apertured plate is controlled by varying a control voltage, which is preferably applied to a conducting layer inside the layered apertured plate. The passage of the ions, which is based on their mobility, can be achieved by a potential difference between outer conductive layers, particularly between conductive layers on the two surfaces of the apertured plate. The transmission current as a function of the control voltage is called the "characteristic" (or "transmission curve"). By selecting the individual layer thicknesses, which can differ greatly from each other, and the aperture profiles, the characteristics for the transmission can be influenced, and particularly such that the characteristic contains a largely linear section on one of its edges.

The apertured plate according to the invention is very robust compared to grids with a large number of thin individual bars, and is much less susceptible to vibrations. It can easily be miniaturized and manufactured with precision using techniques known to a large extent from circuit board manufacture. Even though the maximum transmission corresponds only to around half that of a grid, the apertured plate has unbeatable advantages, particularly for acquiring mobility spectra on the basis of modulation methods.

The invention furthermore provides an ion mobility spectrometer comprising an ion source, a drift region and an ion detector, and methods for its operation, where a gating element according to the invention, comprising a layered apertured plate, is located between the ion source and the drift region.

The gating element comprises a potential generator, which produces a variable control potential, which is preferably applied to an inner electrode layer of the apertured plate in order to control the passage of the ions from the ion source into the drift region. The potential generator here can produce a continuously modulated or pulsed control potential in order to produce a continuously (analog) modulated ion current or an ion pulse into the drift region. Further potential generators can additionally produce fixed potentials, which are applied to outer conductive electrode layers of the apertured plate.

The ion mobility spectrometer according to the invention can operate at atmospheric pressure and can additionally be easily miniaturized, i.e., it can have a volume of less than 500 cm$^3$ and in particular of around 100 cm$^3$ or even less.

A further method according to the invention comprises determining the characteristic of a gating element according to the invention by simulation methods or experimentally, and optimizing the characteristic by varying the parameters of the layered apertured plate, particularly the number of layers, the materials of the layers, the thickness of the layers, and the shapes of the apertures so that the characteristic is linear over as wide an area of a control voltage as possible.

DETAILED DESCRIPTION

Figure 1:
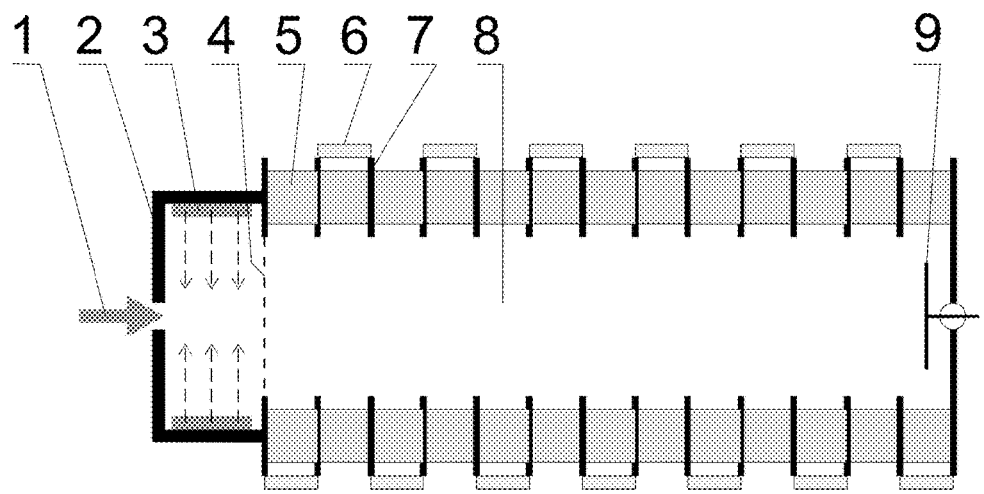
FIG. 1 shows a schematic diagram of an ion mobility spectrometer operated at atmospheric pressure for the detection of pollutants, drugs or explosives, as is commercially available. The schematic representation does not show the weak, internal flow of the collision gas which opposes the direction of the drift. Ambient air with the usual water vapor and the substances to be analyzed (for example, pollutants in the air) enters the ion source housing (2) with the air stream (1). Some air molecules are ionized by the electrons of the beta emitter (3), which comprises of $^{63}$Ni, for example, and react immediately in a complex way with air and water molecules to form complex ions, which usually have one of the forms $(H_2O)_n.OH_3^+$ or $(H_2O)_n.OH^-$. These serve as reactant ions for the ionization of the substances to be analyzed. The ions of the substances being analyzed drift in the ion source (2) toward the gating grid (4); the ion current here can be switched in the form of pulses or modulated by a modulation function. The drift region (8) is surrounded by electrodes (7), which are separated from each other by insulators (5). They are supplied with potentials via a voltage divider comprising individual resistors (6), said potentials generating a uniform electric field in the drift region (8). Drawn by this field, the ions drift through the drift region (8) to the Faraday collector (9), where the variation of the ion current is measured in time.
Figure 2:
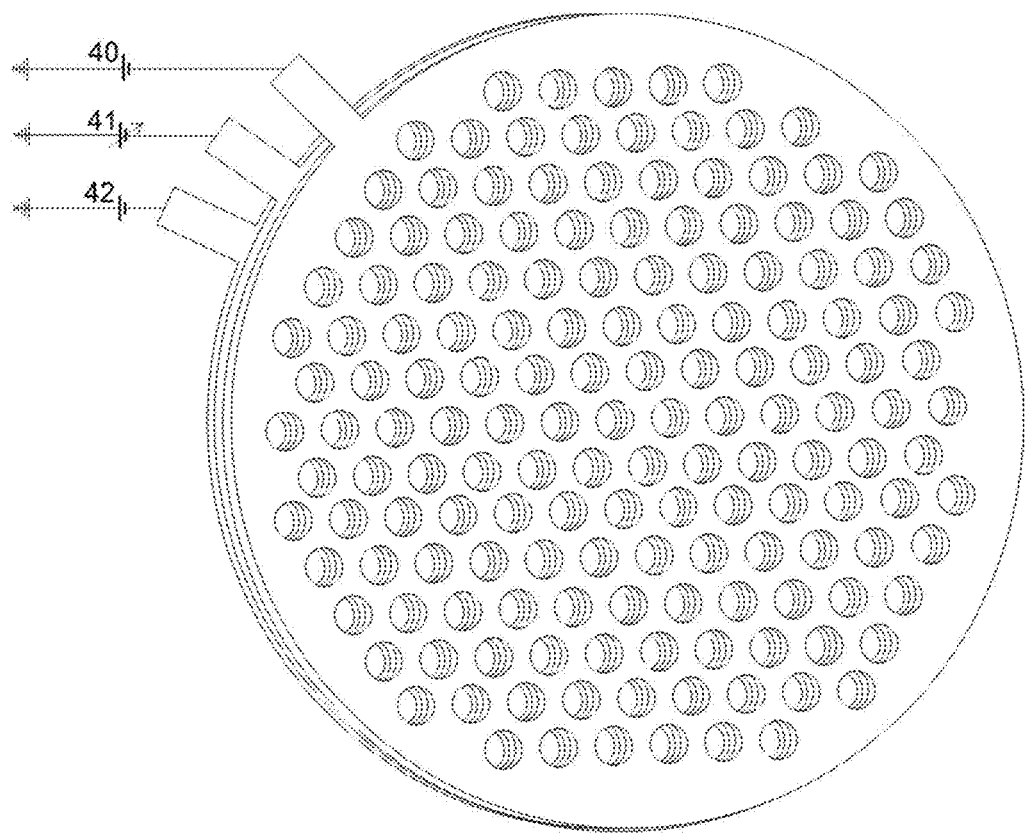
FIG. 2 shows an embodiment of a layered apertured plate which forms the basis of this invention and serves as the gating element for the switching or modulating the ion current instead of the gating grid (4). The apertured plate has five firmly bonded layers, made of alternating conductive and non-conductive (or low-conductivity) material. The apertures are preferably drilled with ultra-short pulse lasers, with only a few seconds being needed to drill all the apertures of an apertured plate. Several such gating elements can be produced in a single process. The layer thicknesses and the aperture profiles (aperture shapes) can be selected so as to produce a favorable characteristic for an analog modulation of the ion current. If optimally selected materials are used, the plate is rugged and easy to handle. A layered apertured plate is less susceptible to vibrations than free-standing wire grids or free-standing layers. The metal layers have tabs for making the contacts. Potential generators (40) and (42) supply fixed voltages for the outer electrode layers, and potential generator (41) supplies a variable voltage for a center electrode layer, which serves as the control electrode.

The invention proposes that, instead of a grid with a large number of thin individual bars (or a series of such grids), a layered apertured plate is used, as shown schematically in FIG. 2. This apertured plate comprises three conductive and two insulating (or low-conductivity) layers, which are arranged alternately. The conductive layers ("electrode layers") have tabs to create the contacts. Such an apertured plate can comprise layers of copper-Kapton-copper-Kapton-copper, or layers of silver-ceramic-silver-ceramic-silver, for example. When copper is used, it is favorable to finish the surfaces which are in contact with the gas with a metal which is more noble, such as gold or chromium. The layers are firmly bonded with each other. Bonding techniques such as calendering or adhesive bonding are known from the production of circuit boards. The surfaces of the ceramic layers can be metallized in advance.

An apertured plate according to the invention can be any shape, for example circular, square or hexagonal, with diameters of four to 15 millimeters. The thickness of the plate is preferably between 50 and 500 micrometers. The apertures can be produced by chemical etching, by ion etching, and particularly by laser drilling, preferably with ultra-short pulse lasers. A femtosecond laser can easily drill several hundred apertures per second, for example, with practically no heat input, which would distort the plate by thermal load. The apertures have practically no burrs and can be produced with different profiles. The apertures in an apertured plate according to the invention can have a diameter of between 50 and 500 micrometers; they can be circular, square or hexagonal, with or without rounded corners. It appears favorable for the aperture diameter to roughly correspond to the depth of the aperture through the plate, but other ratios of diameter and depth are not excluded. The optical transparency of the plate can be selected; it can be around 50%, for example, in which case the area of the apertures corresponds to half the area of the plate. It is also possible to produce plates with greater transparency, whose apertures are arranged like a honeycomb, for example. Overall, a favorable compromise between ion transparency and plate stability must be chosen.

The passage of the ions, which is based on their mobility, can be assisted by a potential difference, which is generated in FIG. 2 by the potential generators (40) and (42) between the outer electrode layers of the apertured plate shown there. The transmission of the ion current through the apertured plate in FIG. 2 can be controlled by varying control voltages of the potential generator (41) at one of the inner electrode layers. In the following investigations, fixed antisymmetric potentials are applied to the outer electrode layers; in addition, weak electric fields are present in the outside region for feeding and extracting ions. In the simulations, a field strength of 300 volts per centimeter is set outside as well as inside the plate. The potential difference is chosen such that the field strength generated between the outer electrode layers corresponds to the field strength in the outside region, thus resulting in a continuous transition between the regions. The transmitted ion current as a function of the control voltage is called the "characteristic" or "transmission curve". It is shown below that the shape of the characteristics can be influenced by the layer thicknesses chosen, which can differ greatly from one another, and by the aperture profiles chosen. In particular, characteristics can be produced with largely straight edges.

In particular, it is possible to select more than just five layers for the plate, for example in order to generate even straighter characteristics for the modulation of the ion currents. With further switching or modulation levels, the temporal course of the ion profile can be influenced, for example to cut off lagging ions during the slow closing with analog modulation. Only results of simulations with five layers are shown in the following, however.

The apertured plate is very robust compared to grids with many, often thin, individually deformable single bars and is less susceptible to vibrations, since it is a compact unit. It can easily be miniaturized and manufactured with precision at low cost and in large numbers with techniques known from circuit board manufacture. Even though the maximum transmission corresponds only to around half that of a grid, the apertured plate has unbeatable advantages, particularly for acquiring mobility spectra on the basis of modulation methods.

Figure 3A:
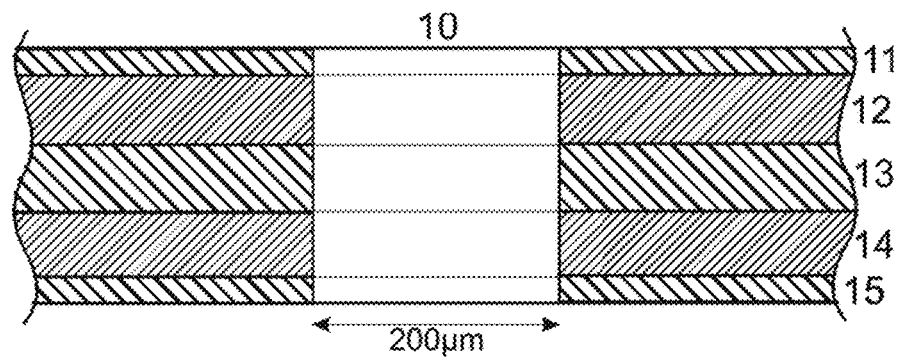
FIG. 3A depicts a single cylindrical aperture (10) of a layered apertured plate which consists of the conductive layers (11), (13), (15) and the non-conductive layers (12) and (14). The layer thicknesses (from top to bottom) are 25, 50, 50, 50 and 25 micrometers; the aperture has a diameter of 200 micrometers.

The passage of the ions through a single hole, as a function of the control voltage at an inner electrode layer, can be simulated with suitable programs or measured experimentally. This results in the characteristic (transmission curve) being obtained as a function of the control voltage. As the starting point for different embodiments, FIG. 3A depicts a single cylindrical aperture (10) of an apertured plate which consists of the three conductive layers (11), (13), (15) and the two non-conductive layers (12) and (14). The layer thicknesses are chosen so as to be symmetric and are 25, 50, 50, 50 and 25 micrometers; the aperture has a diameter of 200 micrometers.

Figure 3B:
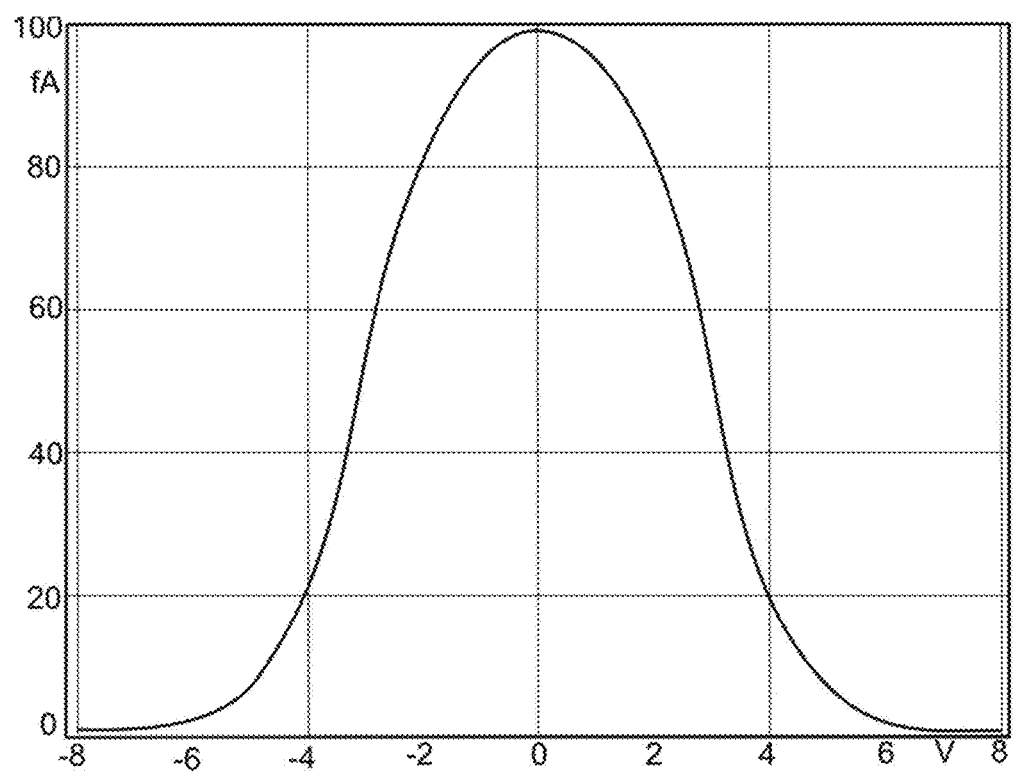
FIG. 3B represents the transmission curve of the individual aperture (10) from FIG. 3A, as obtained by simulation for the ion current in femtoamperes (ordinate) as a function of the control voltage in volts (abscissa) at the electrode (13). The transmission curve (characteristic) has roughly the shape of a Gaussian curve without straight sections on the edges.

FIG. 3B represents the transmission curve of the aperture (10) from FIG. 3A as obtained by simulation for the ion current in femtoamperes (ordinate) as a function of the control voltage in volts (abscissa) at the electrode (13). The transmission curve (characteristic) is symmetric, as expected, and roughly the shape of a Gaussian curve without straight sections on the edges.

Figure 4A:
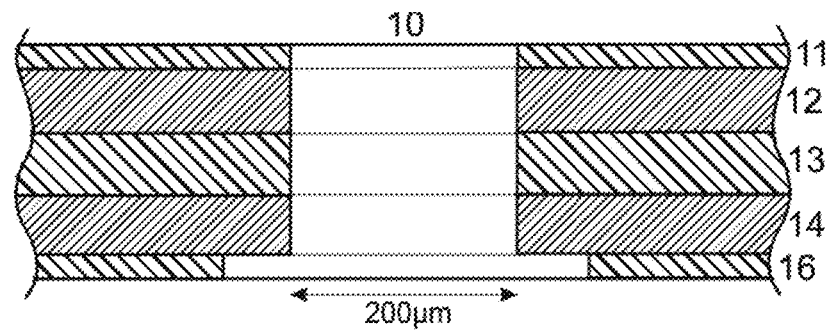
FIG. 4A represents a single aperture (10) of a layered apertured plate, whose conductive layer has a larger diameter where the ions exit and which forms an "eye", so-to-speak.
Figure 4B:
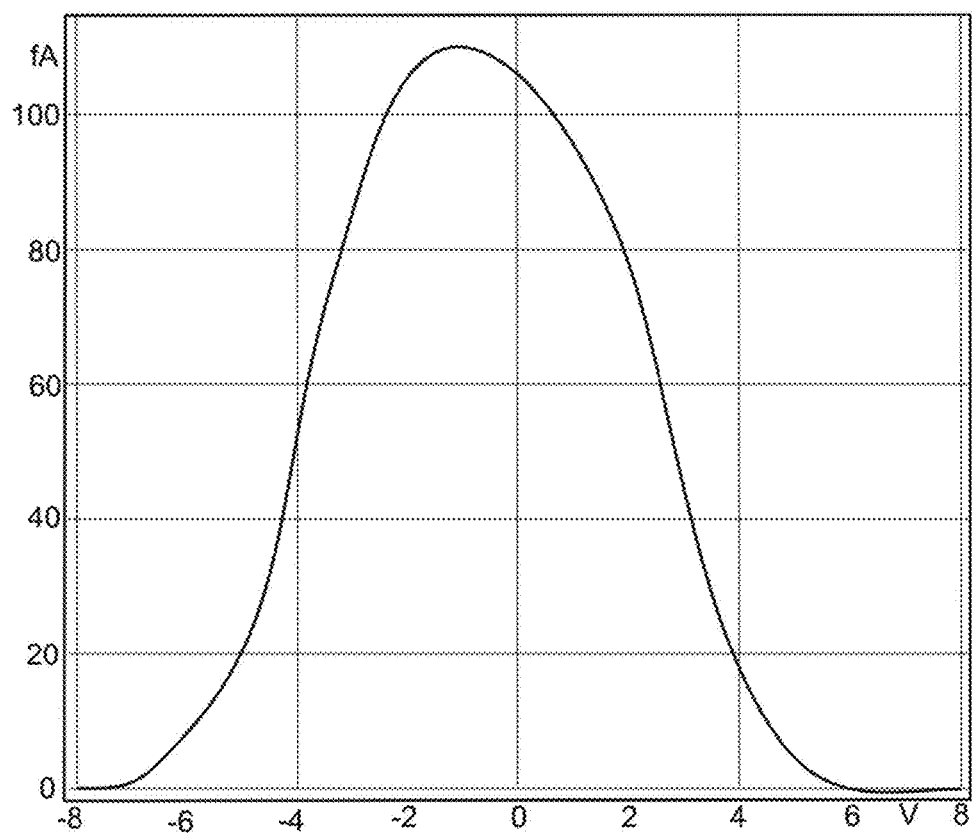
FIG. 4B again shows the transmission curve of the individual aperture (10) from FIG. 4A obtained by simulation. The transmission curve now has a slight asymmetric distortion. The maximum current is roughly 10% higher than in FIG. 3B.

One of the fundamental findings of the invention is that the transmission curve can be changed in various ways with an asymmetric arrangement of the layer thicknesses and the aperture profiles. FIG. 4A therefore illustrates a single hole (10), whose conductive layer has a larger diameter at the ion outlet and forms an "eye", so to speak. FIG. 4B shows that the transmission curve of the single aperture (10) shown in FIG. 4A, obtained by simulation, now has a slight asymmetric distortion, and the maximum current has increased by around 10% compared to the transmission curve shown FIG. 3B.

Figure 5A:
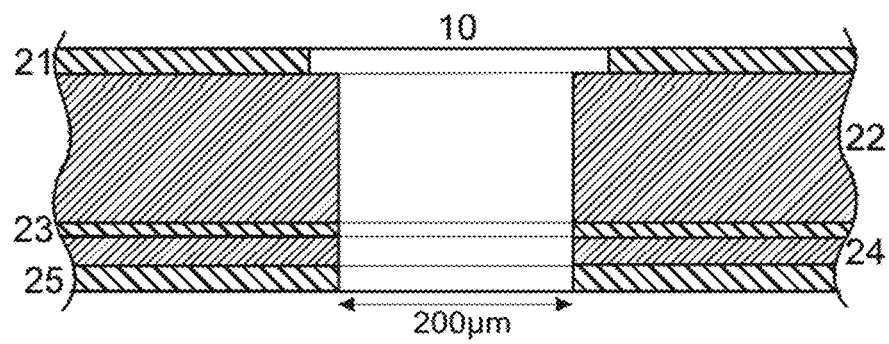
FIG. 5A shows an individual aperture profile of a layered apertured plate, which has an eye at the ion inlet; moreover, the layer thicknesses have been changed: 25, 115, 10, 25 and 25 micrometers.
Figure 5B:
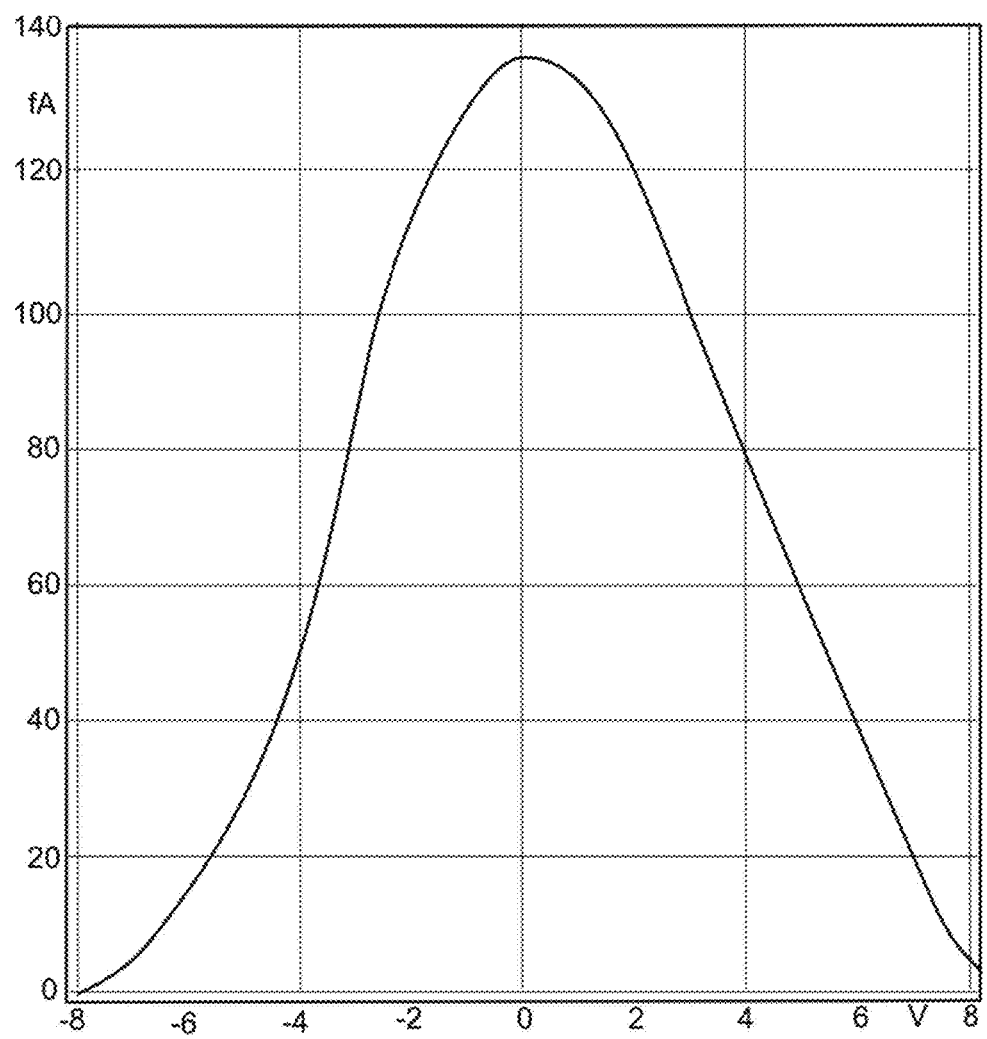
FIG. 5B shows the transmission curve of the individual aperture (10) from FIG. 5A obtained by simulation. The transmission curve now has a long straight edge, which is ideal for a continuous modulation of the ion current without giving rise to harmful sidebands. In addition, the maximum transmission current is roughly 30% higher than in FIG. 3B; in the simulation it amounts to 134 femtoamperes.

A particularly preferred embodiment for a straight characteristic is depicted in FIGS. 5A and 5B. FIG. 5A shows an individual aperture (10) of an apertured plate, which has an eye at the ion inlet; moreover, the layer thicknesses have been changed in an asymmetric way: 25, 115, 10, 25 and 25 micrometers. The simulated transmission curve now has a long straight edge between 1.5 and 7.5 volts of the control voltage, and this edge is ideal for the modulation of the ion current without harmful sidebands resulting. In addition, the maximum transmission current is roughly 30% larger than that in FIG. 3B; in the simulation it is 134 femtoamperes.

The exposed insulator in the eye of the electrode layer (21) in FIG. 5A is unfavorable, however, since it can become electrically charged as a result of impinging ions and thus interferes with the ion transmission. It is therefore advantageous to use not an insulator, but a low-conductivity material for the intermediate layers between the conductive electrode layers. Charging can thus be prevented, since the charges on the surface can flow away. It is also possible to vapor deposit low-conductivity layers onto insulators. It is also known that Kapton can be made slightly conductive by intensive irradiation with UV light or by means of an additional carbon layer on the surface; this effect can be utilized here.

In the previous investigations, the plates are very thin in each case. Although copper foils and Kapton films of the corresponding thicknesses are commercially available, the handling of joining the layers is not very easy without an appropriate technological effort. It shall therefore also be shown that similar results can be achieved with thicker plates and correspondingly larger apertures.

Figure 6A:
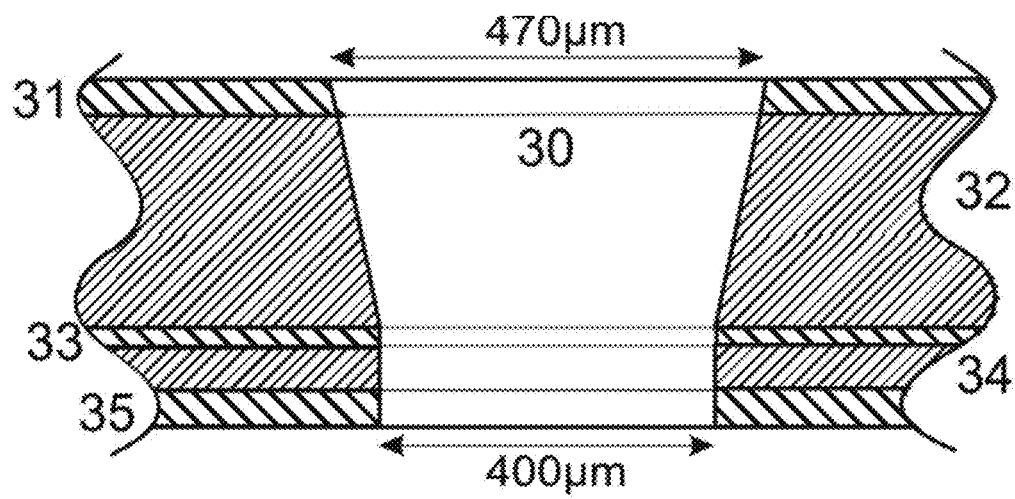
FIG. 6A shows a single aperture profile of an apertured plate that is roughly twice as thick as the one in FIG. 5A, and whose apertures are correspondingly roughly twice as large with a conical profile, as can easily be drilled with an ultra-short pulse laser. The thicknesses of the layers from the top inlet to the bottom outlet are 35, 250, 17, 50 and 35 micrometers; the total thickness is therefore 387 micrometers. Copper foils and Kapton films which can be calendered in the usual way are available for these thicknesses. The single hole has a diameter of 400 micrometers at the outlet, and at the inlet a diameter of 470 micrometers.

FIG. 6A shows an apertured plate which is roughly twice as thick as in the previous embodiments and which has apertures that are twice as big and have a conical profile, as can easily be drilled with a femtosecond laser. The thicknesses of the layers are 35, 250, 17, 50 and 35 micrometers; the total thickness is therefore 387 micrometers. Copper foils and Kapton films, which can be calendered in the usual way, are commercially available for these thicknesses. The Kapton surface in the apertures is slightly conductive. The aperture has a diameter of 400 micrometers at the outlet, and at the inlet a diameter of 470 micrometers.

Figure 6B:
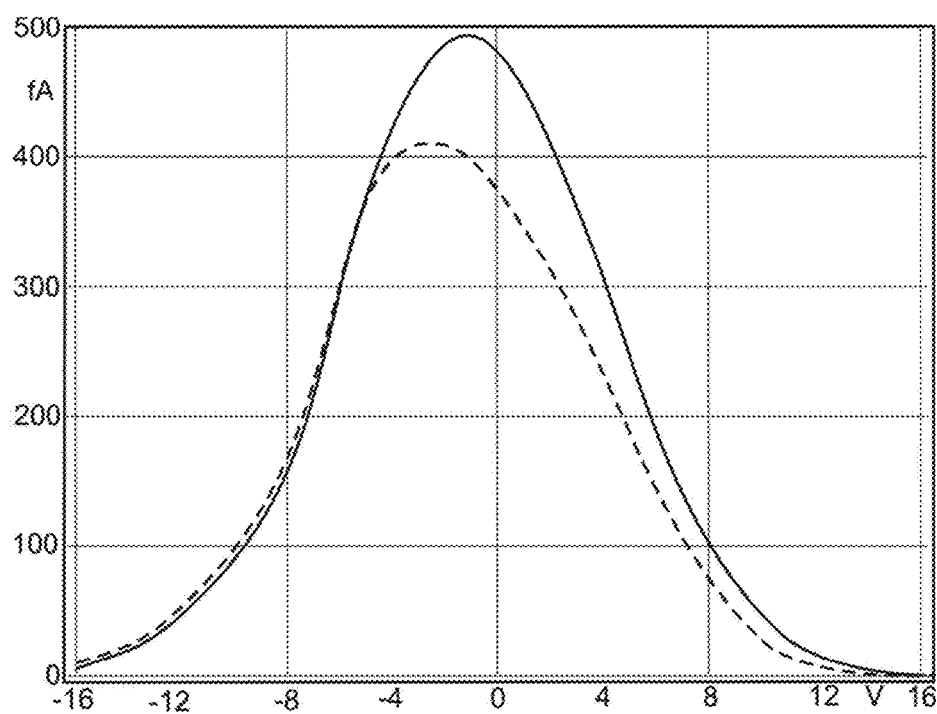
FIG. 6B shows the transmission curve of the individual aperture (10) from FIG. 6A obtained by simulation. The transmission curve shows a much larger ion current of around 500 femtoamperes; the dashed transmission curve is produced with a purely cylindrical hole. The edge is now no longer as linear as in FIG. 5B, but between 0 and 10 volts control voltage, it can still be used for a modulation.

The corresponding transmission curve in FIG. 6B (solid line) now shows a much larger ion current of around 500 femtoamperes. The dashed line shows the transmission curve for a purely cylindrical hole with a diameter of 400 micrometers by way of comparison. The slope of the solid transmission curve is now no longer as ideally linear as the one shown in FIG. 5B, but for a control voltage of between 0 and 10 volts it is still relatively well suited for a modulation, and in any case much better than the transmission curve of the fully symmetric aperture shown in FIG. 3B.

The apertured plate of FIG. 6A is easier to produce than the apertured plates in the previous embodiments because this plate is thicker. The transmission curve depicted in FIG. 6B is therefore a practical compromise. The straightness of the transmission curve can be improved even further by using apertured plates with seven or more layers.

The invention provides a gating element with which preferably the ion current from a continuously operating ion source in a miniaturized ion mobility spectrometer can be analog modulated cleanly and without interfering sidebands, which is mechanically stable, and whose production and handling are simple and low-cost. In particular, different embodiments of the layered apertured plate can produce a favorable characteristic for the modulation of the ion current. The advantageous acquisition of mobility spectra by modulation of the ion current has already been described in the above-referenced patent specification DE 10 2008 015 000 B4 (U. Renner; GB 2 458 368 B; U.S. Pat. No. 8,304,717 B2).

The invention claimed is:

1. A gating element for modulating or switching the ion current in an ion mobility spectrometer, comprising a plate having at least three electrode layers with conductivity of more than $10^6$ S/m and insulating layers with a conductivity of less than $10^5$ S/m between the electrode layers, said layers being bonded to one another, wherein the plate has a plurality of apertures for the passage of ions.

2. The gating element according to claim 1, wherein the plate has a thickness of between 50 and 500 micrometers, and the apertures have a diameter of between 50 and 500 micrometers.

3. The gating element according to claim 1, wherein the apertures are circular, square or hexagonal.

4. The gating element according to claim 1, wherein fixed potential generators supply fixed potentials to two of said electrode layers located at an exterior of the plate, and a variable potential generator supplies a variable control potential to one of said electrode layers located in an interior of the plate, with which the passage of the ions is controlled.

5. The gating element according to claim 4, wherein the ion current is analog modulated by the variable control potential.

6. The gating element according to claim 1, wherein the layer thicknesses and the aperture shapes are selected such that a transmission curve is achieved which contains a largely linear section on one of its edges, which can be used for an interference-free modulation of the ion current.

7. The gating element according to claim 1, wherein the electrode layers are made of metals.

8. The gating element according to claim 1, wherein the insulation layers are made of at least one of Kapton, ceramic or glass.

9. A method for producing a gating element for modulating or switching the ion current in an ion mobility spectrometer, the method comprising:
   providing at least three electrode layers with a conductivity of more than $10^6$ S/m;
   arranging the electrode layers in a parallel configuration with insulating layers separating adjacent electrode layers;
   bonding together the electrode and insulating layers to form a layered structure; and
   drilling apertures in the layered structure.

10. The method according to claim 9 wherein the electrode layers comprise conductive foils.

11. The method according to claim 9 wherein the insulating layers comprise non-conducting or low-conductivity films.

12. The method according to claim 9 wherein bonding together the electrode and insulating layers comprises calendering.

13. The method according to claim 9 wherein bonding together the electrode and insulating layers comprises adhesive bonding.

14. The method according to claim 9 wherein the apertures are laser-drilled.

15. The method according to claim 14 wherein the apertures are drilled using ultra short pulse lasers.

* * * * *